United States Patent [19]

Schütze et al.

[11] Patent Number: 4,922,013

[45] Date of Patent: May 1, 1990

[54] PROCESS FOR THE RACEMIZATION OF OPTICALLY ACTIVE D-2-N-PHENACETYLAMINO-4-METHYL-PHOSPHINOBUTYRIC ACID

[75] Inventors: Rainer Schütze, Kelkheim; Harald Knorr, Frankfurt am Main, both of Fed. Rep. of Germany

[73] Assignee: Hoechst Aktiengesellschaft, Frankfurt am Main, Fed. Rep. of Germany

[21] Appl. No.: 353,613

[22] Filed: May 18, 1989

[30] Foreign Application Priority Data

May 20, 1988 [DE] Fed. Rep. of Germany ....... 3817191

[51] Int. Cl.$^5$ .............................................. C07F 9/30
[52] U.S. Cl. ...................................................... 562/15
[58] Field of Search ........................................... 562/15

[56] References Cited

U.S. PATENT DOCUMENTS

| | | | |
|---|---|---|---|
| 3,796,750 | 3/1974 | Schubel et al. | 260/519 |
| 4,168,963 | 9/1979 | Rupp et al. | 71/86 |
| 4,389,488 | 6/1983 | Grabley et al. | 435/280 |
| 4,602,096 | 7/1986 | Karrenbauer et al. | 548/498 |
| 4,633,086 | 1/1987 | Grabley | 562/401 |
| 4,734,120 | 3/1988 | Kehne et al. | 562/15 |

FOREIGN PATENT DOCUMENTS

| | | |
|---|---|---|
| 1963991 | 7/1971 | Fed. Rep. of Germany . |
| 2717440 | 12/1977 | Fed. Rep. of Germany . |
| 2939269 | 4/1980 | Fed. Rep. of Germany . |
| 3048612 | 7/1982 | Fed. Rep. of Germany . |
| 3334849 | 4/1985 | Fed. Rep. of Germany . |
| 3435095 | 3/1986 | Fed. Rep. of Germany . |
| 3544373 | 6/1987 | Fed. Rep. of Germany ........ 562/15 |
| 3706022 | 9/1988 | Fed. Rep. of Germany ........ 562/15 |
| 2031896 | 4/1980 | United Kingdom . |

*Primary Examiner*—J. E. Evans
*Attorney, Agent, or Firm*—Curtis, Morris & Safford

[57] ABSTRACT

The invention relates to a process for the racemization of D-2-N-phenacetylamino-4-methylphosphinobutyric acid

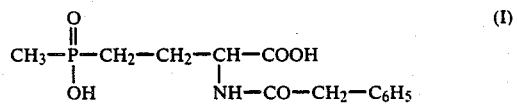

which comprises carrying out the racemization in glacial acetic acid and in the presence of acetic anhydride. The invention makes it possible to convert economically a fairly inactive herbicide into the racemic mixture which contains the highly active L form. The latter can be separated off from the racemized mixture by known methods.

10 Claims, No Drawings

PROCESS FOR THE RACEMIZATION OF OPTICALLY ACTIVE D-2-N-PHENACETYLAMINO-4-METHYLPHOSPHINOBUTYRIC ACID

DL-2-Amino-4-methylphosphinobutyric acid is an amino acid having herbicidal properties (DE-A No. 2,717,440, U.S. Pat. No. 4,168,963) whose ammonium salt is known as a total herbicide under the name glufosinate-ammonium. On synthesis, it is produced as a racemate whose L form is the carrier of the herbicidal activity, whereas the enantiomeric D form only has a small action.

The two enantiomeric forms can be separated by a known method in which the racemate is acylated using phenylacetic acid, and the acyl derivative is cleaved enantioselectively by means of enzymes (DE-A No. 3,048,612, U.S. Pat. No. 4,389,488). This gives a mixture of L-amino acid, phenylacetic acid and D-2-phenacetylamino-4-methylphosphinobutyric acid (I). The latter can be isolated from the product mixture, racemized by a known process (DE-A No. 3,334,849, U.S. Pat. No. 4,638,086) and again fed to the enzymatic cleavage step. The racemization is carried out here by heating with phenylacetic acid in the melt.

Surprisingly, it has now been found that (I) can be racemized particularly well using acetic acid/acetic anhydride.

The invention thus relates to a process for the racemization of D-2-N-phenacetylamino-4-methylphosphinobutyric acid

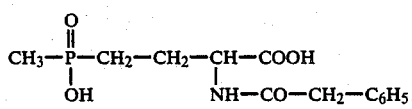

which comprises carrying out the racemization in glacial acetic acid and in the presence of acetic anhydride.

Although the racemization of optically active N-acylamino acids in acetic acid/acetic anhydride has already been disclosed (DE-A No. 1,963,991 (US. Pat. No. 3,796,750), U.S. Pat. No. 2,939,260 (GB-No. 2,031,896), No. 3,435,095 (U.S. Pat. No. 4,602,096) and GB-A No. 1,369,462), these methods always start from the acetyl derivative instead of from the phenacetyl derivative. It could not have been expected that the reaction with the N-phenacetyl derivative of 2-amino-4-methylphosphinobutyric acid would proceed so smoothly; rather, it would have been presumed that a transacylation, i.e. replacement of the phenacetyl radical by an acetyl radical, would occur during the reaction. Transacylations of this type are known from the literature from other systems (A. G. M. Barret, J. Chem. Soc. Perkin Trans. I, 1979, 6, 1629 and J. Fluorine Chem. 3, 167 (1973/74)).

Surprisingly, the phosphinic acid function does not react either. Normally, it is recommended that reactive groups in the amino acid derivatives with functionalized side chains are masked (J. P. Greenstein and M. Winitz, Chemistry of the amino acids, p. 980, Wiley and Sons, New York (1961)).

A second acylation by means of acetic anhydride, as described for amides (Houben-Weyl VIII, p. 709), does not occur either.

The amount of acetic anhydride necessary is at least 1 per cent by weight, based on I, and is preferably 1 to 20% by weight, in particular 5 to 15% by weight. Larger amounts of acetic anhydride can also be used without impairment of the yield (the process can be carried out even in pure acetic anhydride), but it is advantageous, for cost reasons, to use no more acetic anhydride than necessary. The acetic acid : I ratio is preferably in the range from about 2.5:1 to 10:1 (weight/weight). The reaction temperature is preferably between 20° and 150° C., in particular 90° to 115° C.

The racemization is preferably carried out at atmospheric pressure or at a slight excess pressure (less than 2 bar) within from 1 to 120 minutes, depending on the temperature, and in the preferred range within from 5 to 30 minutes.

The process can be carried out either continuously (for example in a flow tube, extruder or in a cascade) or batchwise.

Compared with the known process of DE-A No. 3,334,849 (U.S. Pat. No. 4,638,086), the process according to the invention offers the advantage that lower reaction temperatures can be used and the phenylacetic acid can be replaced by the cheaper and low-boiling acetic acid. In addition, there is no need to work in the melt.

The use of catalytic amounts (1 to 15% by weight, based on I) of acetic anhydride has a further advantage with respect to the economic efficiency of the process.

The process according to the invention is illustrated by the examples below:

EXAMPLE 1

10 g of D-2-N-phenacetylamino-4-methylphosphinobutyric acid are suspended in 30 ml of acetic acid (99.8%), and the mixture is warmed to 115° C. with stirring. 1 g of acetic anhydride is added, and the mixture is stirred at 115° C. for a further 30 minutes. The mixture is cooled to 50° C., and the acetic acid is removed by distillation at 26.7 mbar. The acetic acid removed by distillation can be re-used for the racemization. 50 ml of water are added to the oil which remains, and the mixture is stirred at room temperature for 15 minutes. The water is subsequently stripped off at 60° C. and 26.7 mbar.

9.58 g (96% of theory) of D,L-2-N-phenacetylamino-4-methylphosphinobutyric acid are obtained.

The chemical purity of the starting material and of the racemized product were identical at 98%.

EXAMPLE 2

The procedure as described in Example 1 is followed, but 2 g of acetic anhydride are added and the mixture is stirred at 90° C. for 2 hours. After work-up as in Example 1, 9.5 g (95% theory) of D,L-2-N-phenacetylamino-4-methylphosphinobutyric acid are obtained.

EXAMPLE 3

The procedure as described in Example 1 is followed, but 0.5 g of acetic anhydride are added and the mixture is warmed to 130° C. in a sealed vessel, stirred at this temperature for 30 minutes under an excess pressure and then cooled. After work-up as in Example 1, 9.53 g (95.3% theory) of D,L-2-N-phenacetylamino-4-methylphosphinobutyric acid are obtained.

We claim:

1. A process for the racemization of D-2-N-phenacetylamino-4-methylphosphinobutyric acid

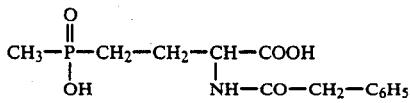

(I)

which comprises carrying out the racemization in glacial acetic acid and in the presence of at least 1 percent by weight of acetic anhydride based on the weight of the compound of the formula I.

2. The process as claimed in claim 1, wherein the amount of acetic anhydride is 1 to 20% by weight, based on the compound of the formula I.

3. The process as claimed in claim 1, wherein the amount of acetic anhydride, based on the compound of the formula I, is 5 to 15 % by weight.

4. The process as claimed in claim 1, wherein the racemization is carried out at between 20° and 150° C.

5. The process as claimed in claim 1, wherein the racemization is carried out at 90° to 115° C.

6. The process as claimed in claim 1, wherein the ratio by weight between glacial acetic acid and the compound of the formula I is 2.5:1 to 10:1.

7. The process as claimed in claim 1, wherein the racemization is carried out at from atmospheric pressure to a pressure of 2 bar.

8. The process as claimed in claim 1, wherein the racemization occurs within from 1 to 120 minutes.

9. The process as claimed in claim 7, wherein the racemization occurs within from 5 to 30 minutes.

10. The process as claimed in claim 1, wherein the amount of acetic anhydride, based on the compound of formula I, is 1 to 20% by weight and the racemization is carried out at between 20° and 150° C.

* * * * *